Figure 1:
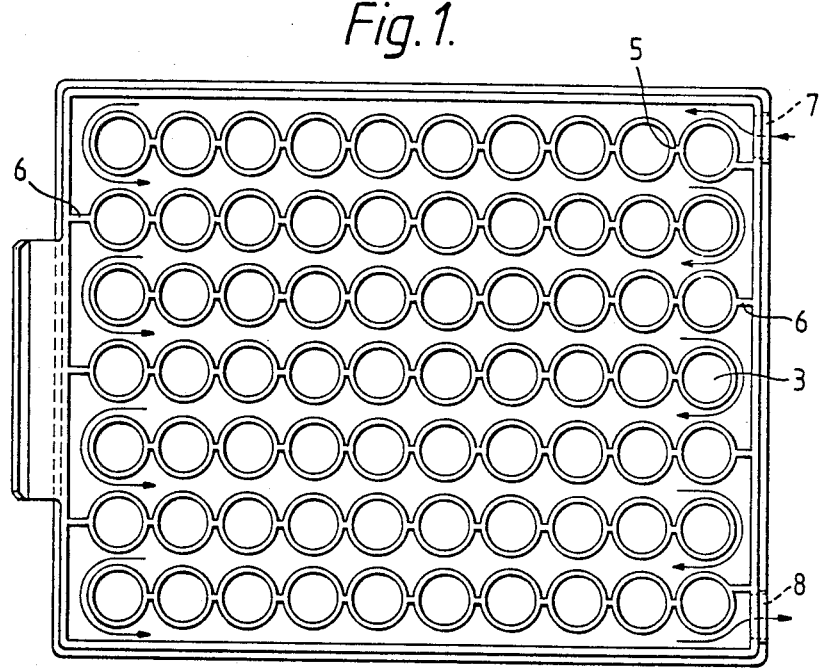

United States Patent [19]

Ekholm et al.

[11] Patent Number: 4,824,791
[45] Date of Patent: Apr. 25, 1989

[54] THERMOSTATED CUVETTE SET

[75] Inventors: Pertti Ekholm; Oili Salmi; Jukka Tuunanen, all of Helsinki; Erkki Vesanen, Kerava, all of Finland

[73] Assignee: Labsystems Oy, Helsinki, Finland

[21] Appl. No.: 34,558

[22] PCT Filed: Jul. 9, 1986

[86] PCT No.: PCT/FI86/00081
§ 371 Date: Mar. 5, 1987
§ 102(e) Date: Mar. 5, 1987

[87] PCT Pub. No.: WO87/00281
PCT Pub. Date: Jan. 15, 1987

[30] Foreign Application Priority Data

Jul. 10, 1985 [FI] Finland .................................. 852736

[51] Int. Cl.⁴ ............................................. G01N 21/03
[52] U.S. Cl. .................................... 436/165; 436/809;
422/58; 422/73; 422/101; 422/102; 356/246; 356/440
[58] Field of Search ...................... 422/58, 61, 73, 99,
422/101, 102, 109; 436/165, 809; 356/244, 246, 440

[56] References Cited

U.S. PATENT DOCUMENTS

| | | | |
|---|---|---|---|
| 3,356,462 | 12/1967 | Cooke et al. | 422/102 |
| 3,505,023 | 4/1970 | Van Damme | 422/102 |
| 3,556,731 | 1/1971 | Martin | 422/102 X |
| 4,431,307 | 2/1984 | Suovaniemi | 422/102 X |
| 4,498,780 | 2/1985 | Banno et al. | 356/244 X |
| 4,545,958 | 10/1985 | Dopatka | 422/102 |

FOREIGN PATENT DOCUMENTS 1486210 9/1977 United Kingdom ................ 422/102

Primary Examiner—Barry S. Richman
Assistant Examiner—Lynn M. Kummert
Attorney, Agent, or Firm—Hopgood, Calimafde, Kalil, Blaustein & Judlowe

[57] ABSTRACT

The invention concerns a thermostated cuvette set in which samples placed in the cuvettes are measured photometrically. Cuvettes of uniform wall thickness are permanently fixed to the bottom of a basin-shaped frame. The cuvettes are connected by partition walls to each other and to the walls of the basin to form arrays of cuvettes defining a path for flow of the thermostating medium. In a preferred embodiment the path is serpentine. The cuvette set also includes at least one inlet opening and at least one outlet opening in the wall of the basin for circulation of the thermostating medium.

13 Claims, 1 Drawing Sheet

THERMOSTATED CUVETTE SET

The subject of the present application is a thermostated cuvette set in which the samples placed in the curvettes are measured photometrically. The cuvette set can be thermostated to the desired temperature by means of a heat transfer medium.

In photometric analyzers, cuvette sets comprising several sample cuvettes are frequently used. In this way the measurements can be carried out rapidly and automatically. In view of accuracy of measurement and of convenience of automation, the most advantageous mode of performance is vertical measurement. This principle of measurement and the cuvette sets for vertical measurement used therein are described, e.g., in the Letters Patent FI No. 57,665 and FI No. 55,093 (equivalent, e.g., to the Letters Patent GB No. 1,486,210) as well as in the U.S. Pat. No. 4,431,307, the cuvettes in the cuvette set described in the latter patent being placed on the bottom of a basin-shaped frame.

In the measurements it is often important that the samples are precisely at a certain temperature. In such a case the cuvette sets with their samples must be thermostated. In prior-art thermostating solutions, e.g., thermostating equipments placed outside the measurement equipment have been used (e.g., "FP-400 INCUBATOR", Labsystems Oy, Helsinki, Finland), in which the cuvette sets can be thermostated before measurement. Heating devices placed stationarily in the measurement equipments themselves are also known, in which the heating takes place by means of heating plates. One apparatus of this sort is described, e.g., in the published Patent Application documents FI No. 843324 (corresponds, e.g., to the published Patent Application EP No. 136,001 A3).

It is also known in prior art to heat photometer cuvette sets by means of a heat transfer liquid. This can be accomplished, e.g., by onto the cuvette set blowing air of uniform temperature.

From the U.S. Pat. No. 4,498,780, an equipment is also known in which a liquid heat transfer medium is used. One equipment in accordance with the patent is provided with a thermostating basin open at the top, onto whose bottom a cuvette set of matrix shape is attached. As to its construction, the cuvette set is a closed piece in which there are cylindrical recesses forming the cuvettes. Moreover, between the rows of cuvettes, there are ducts of rectangular section in which the heat transfer medium flows. The heat transfer duct may also extend partially below the edges of the cuvettes. In this solution, it has, however, not been possible to make sure that the medium is in equally good contact with each cuvette. Moreover, the heat transfer is quite inefficient, because the effective, sufficiently thin heat transfer face adjoining each cuvette is quite little.

The object of the present invention is above all to provide a cuvette set used in photometers and thermostated by means of a medium and in which the transfer of heat into the various cuvettes is uniform and efficient.

The cuvette set in accordance with the invention comprises a basin-shaped frame on whose bottom there are permanently fixed cuvettes whose walls are substantially equally thick. Cuvettes are connected by means of partition walls to each other and to the walls of the basin so that a system of flow ducts is formed in which at least one flow duct by-passes each cuvette. Moreover, at least one inlet opening passes into the flow duct system, and at least one outlet opening passes out of same, so as to circulate the heat transfer medium.

Figure 2:
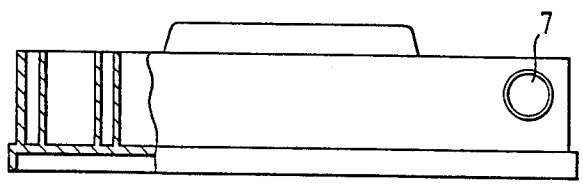
Figure 3:
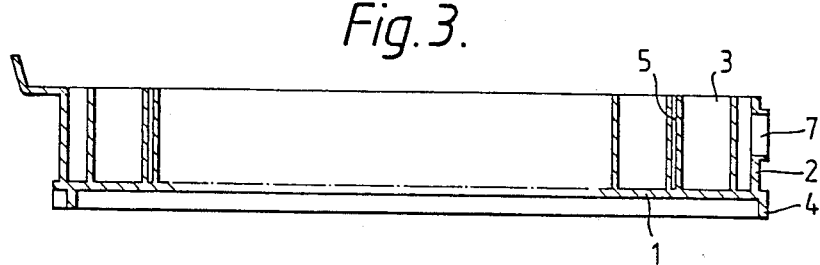
Figure 4:
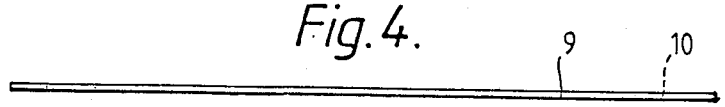

In the following, a preferred embodiment of the invention will be described in further detail. In the drawings related to the description, FIG. 1 shows a cuvette set of rectangular section as viewed from above, FIG. 2 is a side view in section in the transverse direction, FIG. 3 is a side view in section in the longitudinal direction, and FIG. 4 is a side view in section of the cover of the cuvette set in the longitudinal direction.

In the cuvette set for vertical measurement shown in FIG. 1, the bottom 1 and the outer walls 2 of the cuvette set form a basin-shaped frame, on whose bottom the cuvettes 3 shaped as circular cylinders and having walls of uniform thickness are placed in a rectangular matrix $7 \times 10$. The bottom of each cuvette acts as an optical measurement window.

The edge of the bottom of the cuvette set is surrounded by an elevation 4, which prevents scratching of the measurement windows against the base.

The cuvettes in each longitudinal line of cuvettes are interconnected by partition walls 5. An end cuvette in each line is additionally connected to the end by means of an end partition wall 6 so that adjoining lines of cuvettes are always connected to opposite ends.

At the end of the cuvette set in its top portion there is an inlet opening 7, which passes into the space between the first line of cuvettes and the side wall at the end of the line which is provided with an end partition wall. Correspondingly, the same end is provided with an outlet opening 8, which passes into the space between the last line of cuvettes and the side wall. In this way, an unbranched flow duct is provided, which by-passes all the lines of cuvettes from both sides.

The cuvette set further includes a cover 9 covering the basin, which said cover is provided with openings 10 facing each cuvette. In the cover, near the outlet opening, there is a projection, from which the temperature of the liquid present in the flow duct can measured.

When a cuvette set described above is used, samples can be heated or cooled rapidly as required. Thereat, thermostating liquid of the desired temperature is fed in through the inlet opening 7.

The direction of flow of the thermostating liquid can be reversed during the thermostating. In this way a temperature distribution as uniform as possible is obtained even in a large field to be thermostated.

If desired, the thermostating liquid can be coloured, e.g., black, whereby access of light from one cuvette to the adjoining cuvette is eliminated.

Of course, the cuvette set in accordance with the invention may also differ from what is described here as an example. What is essential is that the cuvette set is provided with a flow duct system along which the thermostating medium flows by-passing all the cuvettes.

Thus, for example, the partition walls may be placed in many different ways, and the flow ducts may be branched. The inlet or outlet openings may also be placed in the bottom or cover of the frame. There may also be several openings, in which case the system may have several separate flow ducts.

The cuvette bottoms may also be non-transparent if the light does not have to be passed through the bottom (e.g., measurement of luminescence from above).

Also, the shape of the cuvettes may vary, and they need not be placed in straight lines. If desired, the temperature of the thermostating liquid may be measured at different points of the duct. In principle, the arrangement may also be applied to cuvette sets measured by means of horizontal beams.

In principle, a gas may also be used as the thermostating medium.

What is claimed is:

1. A method for thermostating liquid samples in a cuvette set in which cuvettes of substantially uniform wall thickness are disposed in spaced-apart relationship within a basin-shaped structure having a bottom wall and a side wall, comprising the steps of feeding a thermostated medium through means defining an inlet opening in said side wall into space between said cuvettes and passing said medium past all of said cuvettes and out through means defining an outlet opening in said side wall.

2. A method according to claim 1, wherein said thermostating medium is a colored medium.

3. A method according to claim 1, wherein the direction of flow of said thermostating medium is reversed during thermostating.

4. A cuvette assembly for thermostated photometric analysis comprising in combination cuvettes of substantially uniform wall thickness disposed with spaces therebetween, within a basin-shaped structure having a bottom wall and a side wall, each of said cuvettes having a bottom acting as an optical measurement window and forming part of said basin bottom wall, means defining at least one inlet opening through said side wall communicating with one of said spaces, means defining at least one outlet opening through said side wall communicating with another of said spaces, and partition walls interconnecting said cuvettes to one another and to said side wall to form an array defining a path for fluid flow that extends from said at least one inlet opening to said at least one outlet opening through said spaces for passing fluid by each of said cuvettes.

5. A cuvette assembly according to claim 4, wherein said path for fluid flow passes each of said cuvettes on at least two sides.

6. A cuvette assembly according to claim 4, wherein there is only one inlet opening.

7. A cuvette assembly according to claim 11, wherein there is only one outlet opening.

8. A cuvette assembly according to claim 4 wherein said basin bottom wall is surrounded by an elevation which prevents scratching of said measurement windows.

9. A cuvette assembly according to claim 4 in which said path for fluid flow is unbranched.

10. A cuvette assembly according to claim 4, wherein a cover is disposed over and upon said basin-shaped structure.

11. A cuvette assembly according to claim 10, wherein said cover is provided with at least one temperature detector well projecting into said path.

12. A cuvette assembly for thermostated photometric analysis comprising in combination a tray-like structure having a bottom wall and an encircling side wall, a plurality of individual laterally spaced-apart cuvettes of substantially uniform wall thickness disposed within said tray-like structure upstanding from said bottom wall, partition walls interconnecting each of said plurality of cuvettes with at least one adjacent cuvette, additional partition walls interconnecting certain ones of said plurality of cuvettes with said side wall, means defining at least one inlet opening in said tray-like structure, and means defining at least one outlet opening in said tray-like structure, said plurality of cuvettes being joined by said partition walls so as to form a plurality of spaced-apart serial arrays defining at least one serpentine path for fluid flow between said at least one inlet opening and said at least one outlet opening around said plurality of arrays such that temperature controlled fluid can be passed by all of said plurality of cuvettes around one side of each of said plurality of serial arrays to an other side thereof.

13. A cuvette assembly according to claim 12, wherein said plurality of arrays are each linear and disposed in parallel files joined by said additional partition walls to said side wall alternatingly on opposite sides of said bottom wall so as to define one continuous serpentine path that passes around both sides of each of said plurality of serial arrays of cuvettes.

* * * * *